(12) United States Patent
Kawasaki

(10) Patent No.: US 8,324,374 B2
(45) Date of Patent: Dec. 4, 2012

(54) PROCESS FOR PRODUCTION OF MONOSACCHARIDE AND PROCESS FOR PRODUCTION OF ETHANOL BOTH UTILIZING CELLULOSE-BASED SUBSTANCE

(75) Inventor: Takashi Kawasaki, Yonezawa (JP)

(73) Assignee: Taiyu Kensetsu Kabushiki Kaisha (JP)

( * ) Notice: Subject to any disclaimer, the term of this patent is extended or adjusted under 35 U.S.C. 154(b) by 428 days.

(21) Appl. No.: 12/667,609

(22) PCT Filed: Jul. 2, 2008

(86) PCT No.: PCT/JP2008/062367
§ 371 (c)(1),
(2), (4) Date: Feb. 26, 2010

(87) PCT Pub. No.: WO2009/005168
PCT Pub. Date: Aug. 1, 2009

(65) Prior Publication Data
US 2010/0167368 A1 Jul. 1, 2010

(51) Int. Cl.
*C07H 3/02* (2006.01)
(52) U.S. Cl. .......... 536/56; 536/101; 536/124; 536/127; 435/105
(58) Field of Classification Search .................. None
See application file for complete search history.

(56) References Cited

U.S. PATENT DOCUMENTS

| 5,647,383 | A | 7/1997 | Brodof |
| 5,804,296 | A | 9/1998 | Itoh |
| 2002/0096300 | A1 | 7/2002 | Yamushita |

FOREIGN PATENT DOCUMENTS

| JP | 61261358 | 11/1986 |
| JP | 02101093 | 4/1990 |
| JP | 05140322 | 6/1993 |
| JP | 05140323 | 6/1993 |
| JP | 06012277 | 1/1994 |
| JP | 06226711 | 8/1994 |
| JP | 6279230 | 10/1994 |
| JP | 07118293 | 5/1995 |
| JP | 8157644 | 6/1996 |
| JP | 08157666 | 6/1996 |
| JP | 08225653 | 9/1996 |
| JP | 8260231 | 10/1996 |
| JP | 08299000 | 11/1996 |
| JP | 10066594 | 3/1998 |
| JP | 10110001 | 4/1998 |
| JP | 10251522 | 9/1998 |
| JP | 11036191 | 2/1999 |
| JP | 11313700 | 11/1999 |
| JP | 11325921 | 11/1999 |
| JP | 2002085100 | 3/2002 |
| JP | 2003213584 | 7/2003 |
| JP | 2003342289 | 12/2003 |
| JP | 2005040106 | 2/2005 |
| JP | 2005168335 | 6/2005 |
| JP | 2005239979 | 9/2005 |
| JP | 2005263527 | 9/2005 |
| JP | 2006075007 | 3/2006 |
| JP | 2006238728 | 9/2006 |
| JP | 2006281037 | 10/2006 |
| WO | WO0053832 | 9/2000 |

OTHER PUBLICATIONS

D. Klemm et al. "Degradation of Cellulose", Comprehensive Cellulose Chemistry 1:83-129. (1998).*
Y.H.P. Zhang et al., "A Transition from Cellulose Swelling to Cellulose Dissolution by o-Phosphoric Acid: Evidence from Enzymatic Hydrolysis and Supramolecular Structure", Biomacromolecules, 7:644-648. (2006).*
English Abstract of WO0053832, publication date Sep. 14, 2009.
English Abstract of JP2006-281037, publication date Oct. 19, 2006.
English Abstract of JP2006238728, publication date Sep. 14, 2006.
English Abstract of JP2005263527, publication date Sep. 29, 2005.
English Abstract of JP2005239979, publication date Sep. 8, 2005.
English Abstract of JP2005-168335, publication date Jun. 30, 2005.
English Abstract of JP2003342289, publication date Dec. 3, 2003.
English Abstract of JP2003213584, publication date Jul. 30, 2003.
English Abstract of JP2002085100, publication date Mar. 26, 2002.
English Abstract of JP2006075007, publication date Mar. 23, 2006.
English Abstract of JP2005-040106, publication date Feb. 17, 2005.
English Abstract of JP61261358, publication date Nov. 19, 1986.
English Abstract of JP11325921, publication date Nov 26, 1999.
English Abstract of JP11313700, publication date Nov. 16, 1999.
English Abstract of JP11036191, publication date Feb. 2, 1999.
English Abstract of JP10-251522, publication date Sep. 22, 1998.
English Abstract of JP10-110001, publication date Apr. 28, 1998.
English Abstract of JP08-299000, publication date Nov. 19, 1996.
English Abstract of JP8260231, publication date Oct. 8, 1996.
English Abstract of JP08225653, publication date Sep. 3, 1996.
English Abstract of JP08157666, publication date Jun. 16, 1996.
English Abstract of JP8157644, publication date Jun. 18, 1996.
English Abstract of JP07118293, publication date May 9, 1995.
English Abstract of JP6279230, publication date Oct. 4, 1994.
English Abstract of JP06226711, publication date of Aug. 16, 1994.
English Abstract of JP05140322, publication date of Jun. 8, 1993.

(Continued)

Primary Examiner — Rebecca Prouty
(74) Attorney, Agent, or Firm — Conley Rose, P.C.

(57) ABSTRACT

Disclosed is a novel process which has low facility load, requires a reduced amount of energy, is highly safe, and enables to produce a monosaccharide such as glucose and xylose by decomposing a cellulose-based substance under conditions where a substance used for decomposing the cellulose-based substance (e.g., a solvent, a catalyst) can be separated, collected and re-used readily. Also disclosed is a novel process for producing ethanol from the monosaccharide through ethanol fermentation. Specifically disclosed is a process for producing a monosaccharide, which comprises disaggregating/finely pulverizing a cellulose-based substance, mixing the resulting material with a phosphate solution to disperse the resulting material in the phosphate solution, and decomposing cellulose in the solution at a temperature of 100° C. or lower while irradiating with ultraviolet ray optionally in the presence of titanium dioxide.

6 Claims, No Drawings

OTHER PUBLICATIONS

English Abstract of JP02101093, publication date Apr. 12, 1990.
English Abstract of JP10066594, publication date Mar. 10, 1998.
English Abstract of JP06012277, publication date Jan. 21, 1994.
English Abstract of JP05140323, publication date Jun. 8, 1993.
International Search Report dated Nov. 4, 2008 for PCT/JP2008/062367 (2 pages).

* cited by examiner

PROCESS FOR PRODUCTION OF MONOSACCHARIDE AND PROCESS FOR PRODUCTION OF ETHANOL BOTH UTILIZING CELLULOSE-BASED SUBSTANCE

CROSS-REFERENCE TO RELATED APPLICATIONS

The present application claims the benefit of priority to PCT/JP2008/062367 filed 2 Jul. 2008, which is hereby incorporated herein by reference in its entirety for all purposes, and claims the benefit of priority to Japanese Patent Application No. 2007-175682 filed 3 Jul. 2007, which is also incorporated herein by reference in its entirety for all purposes.

STATEMENT REGARDING FEDERALLY SPONSORED RESEARCH OR DEVELOPMENT

Not applicable.

TECHNICAL FIELD

The invention relates to a field relating to a method for producing a monosaccharide such as glucose and xylose by treating a cellulose-based substance with an acid and ultraviolet radiation and also a method for producing an alcohol by treating the monosaccharide by a conventional technique, for example, with an enzyme.

BACKGROUND ART (Important Facts)

Alcohol fermentation of sugars by enzymes has long been known as a method for producing alcohols.

Alcohol fuels have recently attracted much attention because of situation with energy, and the E3 project in which 3% ethanol is mixed with gasoline has been started in Japan. Appeals to wean ourselves from dependence on fossil fuels have been heard for a long time.

In order to replace petroleum with ethanol, it is necessary to guarantee the availability of large amounts of sugar (glucose, fructose, cane sugar, and the like) as raw material. However, even in the case of sugar cane, the yield of sugar from stems is 10 to 20%, major part of stems and leaves is comprised of lignocellulose, which is difficult to decompose, and it is difficult to produce alcohol therefrom by an enzyme within a short time without other modification.

(Conventional Technology)

Methods for producing glucose and for producing ethanol by decomposing lignocellulose on an industrial scale have recently attracted attention. Typical methods of this type are disclosed in JP-A-61-261358, JP-A-62-79230, JP-A-2-101093, JP-A-5-140322, JP-A-5-140323, JP-A-6-12277, JP-A-6-226711, JP-A-7-118293, JP-A-8-157666, JP-A-8-225653, JP-A-8-260231, JP-A-8-299000, JP-A-10-66594, JP-A-10-110001, JP-A-10-251522, JP-A-11-36191, JP-A-11-325921, JP-A-2002-85100, JP-A-2003-213584, JP-A-2003-342289, JP-A-2005-168335, JP-A-2005-239979, JP-A-2005-40106, JP-A-2005-263527, JP-A-2006-75007, JP-A-2006-281037, International Patent Application Publication WO00-53832, and the like.

Basically, methods of three groups are used: (a) a process of producing ethanol from starch and saccharic starting materials; (b) a process of producing ethanol by hydrolyzing a cellulose-based source material with an acid or the like (including a super/subcritical state) and converting into sugar; and (c) a process of producing ethanol by converting a cellulose-based starting material into sugar by an enzymatic method.

JP-A-8-157644, JP-A-11-36191, and JP-A-8-260231, and WO00-53832 disclose treating cellulose with phosphoric acid and titanium to biodegrade the cellulose. In the processes described in these publications, even when cigarette filters, for example, made of cellulose acetate and the like are discarded and allowed to stay in the natural environment, the risk of environmental pollution is low, and these processes are essentially different from the process in accordance with the present invention by which useful monosaccharides are obtained by decomposition by intensive irradiation of ultraviolet rays.

Thus, the treatment of cellulose with phosphoric acid and titanium oxide imparts the cellulose with photodecomposition ability, but cellulose cannot be completely decomposed in this way under natural conditions, and it can be said that the aforementioned techniques are suitable merely as measures against littering with cigarettes and used to facilitate decomposition with enzymes or microorganisms.

A process of dissolving vegetable fibers in high-concentration phosphoric acid and bringing into contact with a hydrogen halide catalyst is disclosed, for example, in JP-A-8-299000. This process is very dangerous because a halide gas is used. Furthermore, concerns are associated with gas recovery and gas-induced corrosion.

Methods for dissolving lignocellulose that have heretofore been known are disclosed in JP-A-61-261358, JP-A-62-79230, JP-A-2-101093, JP-A-5-140322, JP-A-5-140323, JP-A-6-12277, JP-A-6-226711, and JP-A-7-118293 and in subsequently published JP-A-2000-273183, JP-A-2000-325921, JP-A-2003-342289, JP-A-2006-28040 and the like. With these methods, an organic solvent such as a phenol and an alcohol is added to lignocellulose and heating is conducted at 100° C. to 300° C. The treatment is conducted in a high-pressure pot to prevent the organic solvent from evaporating and scattering, and concerns are associated with ignition.

With respect to JP-A-10-110001, JP-A-10-251522, and JP-A-10-66594, in the process described in JP-A-10-110001, cellulase (enzyme) is used for decomposition into glucose.

In the process described in JP-A-10-251522, lignocellulose is heated and carbonized at 250° C. to 300° C., but the inflammation point of wood is usually about 270° C., the process has to be implemented in an oxygen-free atmosphere, and there is a risk of catching fire in the presence of oxygen.

JP-A-2002-85100 discloses a method for hydrolyzing cellulose with a lanthanoid source and pressurized steam at 200 to 270° C., and JP-A-2006-263527 discloses a method for hydrolyzing cellulose in a super/subcritical state.

JP-A-2005-168335 also discloses a method for converting lignocellulose into sugar by hydrothermal treatment and an enzymatic method, and JP-A-2006-2840 discloses a method by which heating is conducted at 190° C. to 300° C. in an organic solvent with a high boiling point and separation is performed by column chromatography.

JP-A-2005-40106, JP-A-2006-75007 and JP-A-2006-281037 disclose that production of glucose from a cellulose-based substance with concentrated sulfuric acid or diluted sulfuric acid causes problems with subsequent separation of sulfuric acid and corrosion of equipment.

[Patent Document 1] (1) JP-A-61-261358, (2) JP-A-62-79230, (3) JP-A-2-101093, (4) JP-A-5-140322, (5) JP-A-5-140323, (6) JP-A-6-12277, (7) JP-A-6-226711, (8) JP-A-7-118293, (9) JP-A-8-157666, (10) JP-A-8-225653, (11) JP-A-8-260231, (12) JP-A-8-299000, (13) JP-A-10-66594, (14) JP-A-10-110001, (15) JP-A-10-251522, (16)

JP-A-11-36191, (17) JP-A-11-325921, (18) JP-A-2002-85100, (19) JP-A-2003-213584, (20) JP-A-2003-342289, (21) JP-A-2005-168335, (22) JP-A-2005-239979, (23) JP-A-2005-40106, (24) JP-A-2005-263527, (25) JP-A-2006-75007, (26) JP-A-2006-281037, and (27) WO00-53832.

SUMMARY OF THE INVENTION (Object of the Invention)

Therefore, it is an object of the invention to provide improved methods for producing monosaccharide and/or ethanol.

(Features of the Invention)

The inventors have conducted a comprehensive study to attain the above-described objects and discovered that glucose or the like can be produced by decomposing a cellulose-based substance by combined action of hydrolysis with phosphoric acid and photodecomposition. It has also been found that the photodecomposition process is enhanced by titanium dioxide and that the amount of produced glucose/xylose can thus be increased. These findings led to the creation of the present invention.

(Features of the Invention)

The first aspect of the invention is a method for producing a monosaccharide having as the gist thereof a feature of disaggregating and finely pulverizing a cellulose-based substance, mixing and dispersing the disaggregated and finely pulverized cellulose-based substance in a phosphoric acid solution, and decomposing the cellulose under irradiation with ultraviolet rays at a temperature of equal to or lower than 100° C.

The second aspect of the invention is a method for producing ethanol which follows the first aspect of the invention, subjects the monosaccharide to alcohol fermentation by an enzyme.

With the method for producing a monosaccharide and ethanol from a cellulose-based substance in accordance with the present invention that has the above-described features, the cellulose-based substance can be decomposed and a monosaccharide such as glucose and xylose can be obtained with good energy efficiency with a simple equipment and without using a high temperature, a high pressure, or materials that can adversely affect the environment. Furthermore, ethanol can be produced by conventional enzymatic decomposition of the monosaccharide.

In addition, the invention makes it possible to produce polysaccharides and monosaccharides useful as starting materials for chemical reagents and medicines and also to use effectively old paper, dead leaves, waste wood, and rice straws that have been conventionally incinerated as wastes for the production of ethanol as the cellulose-based substances.

DETAILED DESCRIPTION OF THE INVENTIONS

The best or desirable mode for implementing a method for producing a monosaccharide and ethanol by using a cellulose-based substance that has the above-described features will be described below.

The cellulose-based substance used in accordance with the present invention essentially can be any natural substance or processed substance, provided that this substance includes cellulose. For example, starch, paper, wood, rice straw, chaff, old paper, and other cellulose-based substances such as dead leaves, wood from construction wastes, timber from forest thinning, and wind-fallen trees can be used. Further, the cellulose-based substance may also include lignocellulose bonded to lignin and tree bark.

When such cellulose-based substances are treated with phosphoric acid or irradiated with ultraviolet rays, it is preferred that the cellulose-based substances be disaggregated and finely pulverized to facilitate the treatment. For this reason, the cellulose-based substance used in the method in accordance with the present invention is preferably finely pulverized to a size of equal to or less than 0.5 mm.

In accordance with the present invention, these cellulose-based substances are treated with phosphoric acid and irradiated with ultraviolet rays.

It is preferred that phosphoric acid of a high concentration be used. The concentration equal to or higher than 50% is sufficient for practical use, but it is preferred that high-concentration phosphoric acid with a concentration of equal to or higher than 70%, more preferably equal to or higher than 80% be used.

Phosphoric acid with a concentration lower than 50% can be also used, but in this case, the moisture has to be heated or treatment has to be conducted in a dry atmosphere under a reduced pressure.

The treatment temperature of the cellulose-based substances is within a temperature range of from 30° C. to less than 100° C., preferably 40° C. to 80° C., even more preferably 40° C. to 60° C.

Where the temperature is equal to or higher than 100° C., the cellulose-based substances are carbonized without decomposing to levoglucosan and cannot be decomposed into a monosaccharide which is the object of the present invention. Further, it is preferred that the decomposition reaction of the cellulose-based substances be conducted in a dry atmosphere. This is to remove the moisture contained in the phosphoric acid and enhance the reaction. The dry atmosphere is obtained, for example, by using a desiccating agent in a drying machine or conducting heating under a reduced pressure.

In the method in accordance with the present invention, the cellulose-based substance is decomposed by treatment with phosphoric acid and irradiation with ultraviolet rays, and the cellulose-based substance can be decomposed into a monosaccharide such as glucose and xylose, and this decomposition reaction can be accelerated when conducted in the presence of titanium dioxide.

The crystal structure of titanium dioxide can be generally classified into rutile type and anatase type. The activity of anatase-type titanium oxide under light irradiation such as ultraviolet rays is much higher than that of rutile-type titanium oxide. For this reason, using the anatase-type titanium oxide is preferred for increasing the photodecomposition ability, but the rutile-type titanium oxide is not disallowed, and the reactivity can be increased even with the rutile-type titanium oxide depending on increase of the ultraviolet lamp illumination intensity, selection of a different wavelength of the ultraviolet rays lamp (lamps of a large number of kinds are produced by Phillips) or irradiation method.

Further, a titanium dioxide catalyst for visible radiation has also been developed, and not only the lamp, but titanium dioxide also can be changed.

The specific surface area and particle size of titanium dioxide also greatly affect the decomposition ability under irradiation with ultraviolet rays. Thus, as the particle size of titanium oxide decreases and specific surface area increases, the degree of activation of titanium dioxide caused by light irradiation such as ultraviolet rays per unit weight can be increased.

This is because the photodecomposition reaction is induced by ultraviolet rays only on the surface of the titanium dioxide that is in contact with the cellulose-based substance, and the increase in contact surface area affects the reaction rate.

For this reason, where titanium dioxide with a small particle size and a large specific surface area is used, the decomposition ability of the cellulose-based substance can be increased with a small addition amount.

(1) The specific surface area of titanium dioxide is equal to or greater than 20 $m^2/g$, preferably 60 to about 150 $m^2/g$, as measured by an air permeation method (Blaine value), and the specific surface area of commercial reagents is most often 50 $m^2/g$ to about 150 $m^2/g$.

(2) The average size of primary particles of titanium dioxide, as measured by a laser microsizer, is 0.002 μm to 0.07 μm, preferably 0.01 μm to about 0.05 μm; the reagents in most cases have an average size of primary particles of 0.005 μm to 0.05 μm.

Titanium dioxide used in accordance with the present invention may have either property from among the above-described (1) specific surface area and (2) average particle diameter, but it is preferred that titanium dioxide be used that has both properties from among the above-described both (1) specific surface area and (2) average particle diameter.

Such titanium dioxide has (3) a specific surface area of equal to or greater than 30 $m^2/g$ and a primary particle size of 0.002 μm to 0.07 μm (for example, 0.002 μm to 0.05 μm), more preferably a specific surface area of 60 $m^2/g$ to 150 $m^2/g$ and a primary particle size of 0.01 μm to 0.05 μm.

However, the contact surface area with cellulose can be also increased by using particles with a size equal to or greater than 0.05 μm, for example about 0.1 μm, admixing 20 parts or more to phosphoric acid, and irradiating with ultraviolet rays under stirring, and such a method also facilitates the separation and recovery (filtration) of titanium dioxide located in phosphoric acid.

As described hereinabove, in the method in accordance with the present invention, the phosphoric acid used preferably has a high concentration, but when cellulose is treated with low-concentration phosphoric acid (a case in which heating is conducted and moisture is evaporated), titanium dioxide is preferably surface treated with an organic substance and/or inorganic substance to increase photodecomposition ability and dispersion ability thereof. The preferred treatment agent includes at least one component selected from among phosphorus compounds, polyhydric alcohols, and amino acids. It is especially preferred that titanium dioxide be used that has been surface treated with a combination of a phosphorus compound and at least one component selected from polyhydric alcohols and amino acids, but components that can be decomposed by a phosphoric acid solution are excluded.

Titanium dioxide subjected to surface treatment with such a surface treatment agent has high dispersivity, the usable surface area thereof per unit weight increases, and photodecomposition ability can be increased.

With the titanium dioxide that has been surface treated with the above-described components, activity of the titanium dioxide can be effectively used. Therefore, by contrast with the above-described titanium dioxide, the specific surface area and/or average particle size of primary particles are not required to be within the above-described ranges.

Examples of the aforementioned phosphorus compounds include phosphorus oxide, phosphoric acids such as hypophosphorous acid, phosphorous acid, hypophosphoric acid, orthophosphoric acid, pyrophosphoric acid, triphosphoric acid, metaphosphoric acid, and polyphosphoric acid, salts thereof, phosphonium salts, and also phosphines and phosphoric acid esters.

The preferred phosphorus compounds include hydrophilic or water-soluble compounds, for example, phosphorus oxide such as phosphorus pentoxide, phosphoric acid, and salts thereof. Phosphoric acid salts include alkali metal salts such as salts of sodium and potassium and ammonium salts. These phosphorus compounds can be used individually or in combinations of two or more thereof.

Most of the aforementioned surface treatment agents are compounds with high safety with respect to humans, for example, compounds that have been certified as edible additives. Examples of such compounds include phosphoric acid and salts thereof such as sodium metaphosphate and sodium pyrophosphate.

Components representing the surface treatment agents may be used individually or in combinations of two or more thereof and preferred surface treatment agent includes titanium dioxide hydrophilized by a phosphorus compound such as phosphoric acid or a salt thereof. Further, when titanium dioxide is dispersed, a surfactant, a metal soap or the like may be used.

The surface treatment of the titanium dioxide can be conducted by the usually used method, for example, by immersing titanium dioxide into a solution including the above-described component, using a Nauta mixer manufactured by Hosokawa Micron KK for titanium dioxide, and spraying, but the effect is obtained when the treatment amount of the phosphorus compound is about 0.5 to 5 parts by weight per 100 parts by weight of titanium oxide.

Titanium dioxide may support a metal catalyst to increase activity induced by light irradiation and raise the decomposition efficiency of the cellulose-based substance. Examples of transition metals include Zr, V, Cr, Mo, Mn, Fe, Ru, Co, Rh, Ni, Pd, Pt, Cu, Ag, and Au, and Pd, Pt, and Au are preferred. These metals may be supported in the form of halides such as chlorides, and also oxides, complexes, and the like.

The supported amount of the metal or a compound thereof on 100 parts by weight of titanium dioxide is about 0.01 to 5 parts by weight, as a metal.

The amount of titanium dioxide admixed to the cellulose-based substance is most often 0.01 to 20 parts by weight, preferably 0.25 to 5 parts by weight per 100 parts by weight of the cellulose.

This is because where the contained amount of titanium dioxide is less than 0.01 part by weight, photodecomposition ability is not raised sufficiently, and where the contained amount of titanium dioxide exceeds 20 parts by weight, hiding ability of titanium dioxide increases and transmissivity of ultraviolet rays can be decreased.

In some cases, the above-described titanium dioxide can be dispersed from the very beginning in the cellulose-based substance by a usually used method. For example, a mixture of the cellulose-based substance and titanium dioxide can be dissolved, mixed, and dispersed in an aqueous solution of phosphoric acid, or titanium dioxide can be dispersed in a dry state of the cellulose-based substance. A variety of mixing dispersers can be used in this process, for example, a melting mixer such as a kneader, and a disperser such as a ball mill, a rod mill, and an ultrasound disperser.

Where titanium dioxide subjected to the above-described hydrophilic surface treatment is used, the titanium dioxide can be easily dispersed in the cellulose-based substance and dispersion stability can be increased.

It is preferred that the above-described anatase-type titanium oxide be contained in the cellulose ester composition in accordance with the present invention, but rutile-type titanium oxide may be also contained.

Titanium dioxide has been used as a pigment and also in food products and cosmetics and has a high level of safety with respect to a human body.

The photodecomposition reaction of the cellulose-based substrate in accordance with the present invention can be enhanced not only by the titanium dioxide catalyst, but also by the presence of a metal. Stainless steel is preferred as the metal, and using a reaction container made from stainless steel makes it possible to utilize the catalytic action thereof.

Further, a method for conducting a decomposition reaction induced by ultraviolet radiation in the presence of titanium dioxide can be implemented by attaching titanium dioxide to a coating film, providing the coating film surface with concavities and convexities, creating a thin flow of a fluid prepared by dispersing a finely pulverized cellulose-based substance in a phosphoric acid, while ensuring that the location of fluid is changed at all times between the surface and the inner zones, irradiating the fluid with ultraviolet rays and uniformly enhancing the decomposition reaction enhanced by titanium dioxide.

It is also possible to use a method by which a fluid prepared by dispersing a finely pulverized cellulose-based substance in a phosphoric acid is caused to pass through a net having titanium oxide fixedly attached thereto and the fluid is irradiated by ultraviolet rays, or a method by which a cellulose substance is finely pulverized, dispersed together with a phosphoric acid solution and titanium dioxide, and the resultant fluid is irradiated from outside or inside with ultraviolet rays.

Further, a method can be also used by which a cellulose-based substance is finely pulverized, in a reaction tank in a batch mode, dispersed in phosphoric acid and a titanium dioxide powder, and irradiated from the inside or surface or from both the inside and the surface with ultraviolet rays under stirring.

Another possible method includes dispersing a pulverized cellulose-based substance with titanium dioxide in a low-concentration aqueous solution of phosphoric acid (a dispersant can be also added), irradiating with ultraviolet rays under heating, evaporating water and concentrating the phosphoric acid, and conducting the reaction, while raising the concentration of phosphoric acid.

Yet another possible method includes immersing a cellulose-based substance into high-concentration phosphoric acid, causing gelling and swelling, separating extra phosphoric acid by filtration, mixing titanium dioxide with the gel substance obtained, producing a paste, and irradiating with ultraviolet rays under heating.

In accordance with the present invention, it is not necessary to conduct irradiation of ultraviolet rays with dehydration under heating at the same time. Thus, irradiation with ultraviolet rays may be followed by drying. In addition, a method can be used by which a cellulose-based substance is finely pulverized, mixed with a fine powder of titanium oxide, and dispersed in phosphoric acid, ultraviolet irradiation is conducted, while spraying the dispersion into a mist, and glucose is produced, while concentrating the phosphoric acid by blowing hot air and enhancing the hydrolysis.

The present invention will be described below in greater detail.

[Reference Test 1]

Cellulose (JK Wipe: test paper towels manufactured by Jujo Kimberly) was impregnated with a solution prepared by dispersing titanium dioxide in a 10% aqueous solution of ammonium phosphate, evaporation and drying were conducted at 100° C., ammonia of ammonium phosphate was removed, and the reaction was enhanced by concentrating phosphoric acid. As a result, the cellulose was converted into a brittle carbonized sheet.

[Reference Test 2]

Cellulose (JK Wipe: test paper towels manufactured by Jujo Kimberly) was impregnated with a solution prepared by dispersing titanium dioxide in a 10% aqueous solution of phosphoric acid, and the reaction was conducted in a drying unit at 80° C. As a result, the cellulose was converted into a carbonized sheet.

[Reference Test 3]

Cellulose (JK Wipe: test paper towels manufactured by Jujo Kimberly) was impregnated with a solution prepared by dispersing titanium dioxide in a 10% aqueous solution of phosphoric acid, placed on a stainless steel mesh (mesh for water draining that is designed for a kitchen; spacing between the vertical wires is 1 cm), and the reaction was conducted for 12 H in a drying unit at 80° C. The cellulose was partially carbonized, grease-like black liquefied state was assumed in the four corners that sagged down, portions that were in contact with the SUS net assumed a grease-like form, and the remaining section became a carbonized sheet. Accordingly, a zone with a width of 1 cm was cut out.

[Reference Test 4]

JK Wipe was immersed in 85% phosphoric acid (high-concentration phosphoric acid manufactured by Kanto Kagaku KK; same hereinbelow) (20 cc phosphoric acid for 1.12 g) and pasted onto a stainless palette. The JK Wipe treated overnight under ultraviolet radiation assumed a transparent semi-liquid state (paste- or grease-like sticky form). Drying at 40° C. started liquefaction in about 1 h, a fluid state was assumed in 4 h, a light-brown solution was obtained in 6 h, and flowability was then further increased.

[Reference Test 5]

JK Wipe (1.12 g) was immersed in 85% phosphoric acid (20 cc) and pasted onto a stainless palette (SUS). Titanium dioxide (about 0.05 g) was uniformly sprinkled over the palette. The JK Wipe treated overnight under ultraviolet ray radiation assumed a transparent solution-like state (not a gel). It was then placed in a drying unit at 40° C., liquefaction was started in about 30 min, a fluid state was assumed in 1 h, a light-brown solution was obtained in 2 h, and flowability was then further increased.

[Reference Test 6]

JK Wipe (1.12 g) was immersed in 85% phosphoric acid (20 cc). The JK Wipe uniformly studded with titanium dioxide and treated overnight under ultraviolet radiation on a palette made of a PP material was gelled (rather than liquefied), by contrast with that treated on the SUS palette. The reaction was then conducted for 12 H in a drying unit at 40° C., and the entire sample assumed a highly viscous solution state of brown color. A dissolved state was maintained even after the addition of water.

When JK Wipe (1.12 g) was immersed in 85% phosphoric acid (20 cc) on palette made of a PP material and no ultraviolet irradiation was conducted, a gelled state was obtained. When the reaction was then conducted for 12 H in a drying unit at 40° C., the entire sample assumed a highly viscous solution state of brown color. However, when water was added, a gel-like substance could be seen.

[Reference Test 7]

Then rice straws (lignocellulose) were disaggregated, fibers were filtered via a sieve having 0.5 mm openings, the fibers on the sieve were dried, and placed on a stainless steel palette, the dried fibers (1.12 g) were then immersed in 85% phosphoric acid (20 cc), and allowed to stay overnight. The next day, about half appeared dissolved and the remaining fibers were also partially dissolved and reduced in thickness.

When the semi-dissolved rice straws were treated overnight at 40° C. in a drying unit, most of them were dissolved, however, thick portions of some fibers remained undissolved.

Then, rice straws were disaggregated and filtered via a sieve having 0.5 mm openings. The fibers on the sieve were dried, placed on a stainless steel palette, and immersed in 85% phosphoric acid (20 cc phosphoric acid for 1.12 g). Titanium dioxide was then sprinkled over the fibers and the fibers were allowed to stay overnight under irradiation with ultraviolet rays. The next day, about 80% were dissolved, and the remaining fibers were also partially dissolved and reduced in thickness.

The semi-dissolved rice straws were completely dissolved when treated overnight at 40° C. in a drying unit (no undissolved fibers remained).

Then, rice straws were disaggregated, and the fibers were filtered via a sieve having 0.5 mm openings. The fibers remaining on a sieve having 0.15 mm openings under—said sieve were dried, and 2 g of the dried fibers were dispersed in 250 cc of 85% phosphoric acid and irradiated with ultraviolet rays under stirring in a drying unit (made from 18-8 SUS) at 40° C. The dissolution was completed in 4 h.

Further, rice straws were disaggregated, and the fibers were filtered via a sieve having 0.5 mm openings. The fibers remaining on a sieve having 0.15 mm openings under said sieve were dried, and 4 g of the dried fibers were dispersed in 250 cc of 85% phosphoric acid and 0.5 g of titanium dioxide and irradiated with ultraviolet rays under stirring in a drying unit (made from 18-8 SUS) at 60° C. The dissolution was completed in 3 h.

The above-described results demonstrated that the rice straws are dissolved within a short time into glucose, xylose and the like when rice straws are finely disaggregated (size of 0.5 mm or less), the ratio of high-concentration phosphoric acid is increased (1:40 or more), irradiation with ultraviolet rays is conducted, while the sample is in contact with stainless steel and titanium dioxide, and stirring and drying are conducted at 40° C. to 60° C.

[Test 1]

Where cellulose (paper: JK Wipe=test paper towels manufactured by Jujo Kimberly; pure virgin pulp) is immersed in high-concentration phosphoric acid and allowed to stay indoors, the cellulose absorbs moisture from the air and swells, thereby forming a gel. However, the sample (paper) irradiated with ultraviolet rays is converted into a somewhat yellowish paste.

Where a total of 1.12 g (dry weight) of cellulose (JK Wipe=test paper towels manufactured by Jujo Kimberly, pure virgin pulp) is immersed in 20 cc of 85% phosphoric acid at a low temperature (about 5° C.) and irradiated for 12 h with a 10 W antibacterial lamp produced by Toshiba, the cellulose assumes a semitransparent state and a part thereof is liquefied (is not converted into a gel).

Where the treated cellulose is dried in a drying unit at 40° C. (silica gel is introduced to obtain a dry state), liquefaction starts in about 1 h, a fluid state is assumed in 4 h, a light-brown solution is obtained in 6 h, and flowability is then further increased.

[Test 2]

Where 1.12 g of cellulose (JK Wipe) is similarly immersed at a low temperature (about 5° C.) in 20 cc of 85% phosphoric acid having dispersed therein 0.05 g of anatase-type titanium dioxide (first grade reagent) and irradiated for 12 h with a 10 W antibacterial lamp produced by Toshiba, the cellulose assumes a semitransparent state, and liquefaction in the process in which titanium dioxide is added advances further compared with that in the case in which no titanium dioxide is added.

Where the treated cellulose is dried in a drying unit at 40° C. (silica gel is introduced to obtain a dry state), liquefaction starts in about 30 min, a fluid state is assumed in 1 h, a light-brown solution is obtained in 2 h, and flowability is then further increased.

[Test 3]

Lignocellulose (rice straws) are cut to 2 cm, disaggregated and fibrillated in a mixer. A net-like configuration is obtained with a sieve having 0.5-mm openings and the fibers are dried. Then, 1.5 g of the fibers are immersed in 20 cc of 85% phosphoric acid having 0.05 g of anatase-type titanium dioxide (first grade reagent) dispersed therein, and irradiated for 12 h with a 10 W antibacterial lamp produced by Toshiba. As a result, the rice straws become a yellow-white grease (paste) state, the surface being a yellow transparent liquid.

In a case where no titanium dioxide is added to lignocellulose, the decomposition leaves a sticky surface, while retaining a net-like configuration, and a state that can be represented by dissolution or gelling is not assumed.

Where lignocellulose to which titanium dioxide had been added and which had been irradiated with ultraviolet rays was introduced in the drying unit at 40° C. and dried for 4 h, the sample having titanium dioxide admixed thereto was liquefied, whereas the sample to which titanium dioxide had not been added was in a gelled state with fibers remaining therein Where titanium dioxide was thereafter added to the sample to which titanium dioxide had not been added, irradiation with ultraviolet rays was conduced for 4 h, and then drying was conducted at 40° C., liquefaction took place (decomposition occurred even though the irradiation with ultraviolet rays and heating were not conducted at the same time).

In a case where the drying temperature was 60° C., a brown liquid was obtained in 1 h, that is, in about half the treatment time of the cellulose (JK Wipe), and a state with high flowability was attained.

It was revealed by this test that, whether the decomposition was completed or not was determined such that, where an equal amount of water is added to the fluidized phosphoric acid treatment liquid, a gel is obtained if the decomposition has not ended, but no gelling occurs in the case of solution in which the decomposition has ended. It is possible to reheat the solution in which the reaction has not ended, raise the concentration of phosphoric acid, and enhance the reaction by admixing titanium dioxide and conducting irradiation with ultraviolet rays, in order to complete the reaction.

Precipitation and separation can be then conducted by mixing slaked lime, aluminum hydroxide, or iron hydroxide to the phosphoric acid solution in which the reaction has ended and which includes the decomposed cellulose (glucose and the like), neutralizing the solution, and converting the phosphoric acid component into calcium phosphate (aluminum phosphate, iron phosphate).

It is thereafter possible to convert the separated calcium phosphate into an acidic form by the well-known technique, redissolve it, separate into calcium carbonate and phosphoric acid by using carbon dioxide, reuse the phosphoric acid, dehydrate and dry the separated calcium carbonate, produce quicklime by overheating, produce slaked lime by reaction with water, and reuse both the phosphoric acid and the lime Phosphoric acid and titanium dioxide can be also separated by using reverse osmosis membrane and can be reused to decompose cellulose.

Further, a separation method using a column filled with a special cation exchange resin (JP-A-2005-239979) and a separation method in which column chromatography is used such as silica gel chromatography and an eluate of elution fraction of anhydrosaccharide is distilled off (JP-A-2006-28040) are known.

Further, in some cases an extremely small amount of phosphoric acid is also admixed to the glucose solution from which phosphoric acid has been separated by reverse osmosis membrane or the like.

However, because phosphoric acid serves as an activation energy of enzymes in the subsequent alcohol fermentation, the phosphoric acid does not adversely affect the enzyme activity, as sulfuric acid.

A very small amount of phosphoric acid is also contained in the residue that remained untreated, but this residue can be reused as a fertilizer for plants and treated. Furthermore, where heating is thereafter conducted at a temperature of equal to or higher than 100° C. in a state in which phosphoric acid is included, the cellulose-based substance residue is carbonized and can be used for an adsorbers or, when treated for 1 min at 450° C., can be used as an electromagnetic wave absorbing material.

Examples are shown below to illustrate the invention in greater detail, but it goes without saying that the features of the invention are not limited to these examples.

Example 1

A total of 20 cc of 89% phosphoric acid (high-concentration phosphoric acid manufactured by Rasa Kogyo KK; same hereinbelow) was added to 1.12 g (dry weight) of one sheet of paper-like cellulose (JK Wipe), and then irradiation with ultraviolet rays was conduced at ambient temperature (5° C.) for 24 h with a 10 W antibacterial lamp produced by Toshiba.

The sample was then placed in a drier at 40° C. having silica gel placed therein and dried by heating for 24 h. This procedure of sample preparation was repeated 5 times and a total of 300 cc (solid fraction 30 g) was produced. The analytical values of the sample are shown in Table 1 below.

Example 2

A total of 20 cc of 85% phosphoric acid was added to 1.12 g (dry weight) of one sheet of paper-like cellulose (JK Wipe), about 0.05 g of titanium dioxide was applied to the surface of the paper-like cellulose, and irradiation with ultraviolet rays was conducted at ambient temperature (5° C.) for 24 h with a 10 W antibacterial lamp produced by Toshiba.

The sample was then placed in a drier at 40° C. having silica gel placed therein and dried by heating for 24 h. This procedure of sample preparation was repeated 5 times and a total of 300 cc (solid fraction 30 g) was produced. The analytical values of the sample are shown in Table 1 below.

Example 3

A total of 2 g of rice straws were placed together with water into a mixer and disaggregated. The disaggregated fibers were filtered with a sieve and dried. A total of 20 cc of 85% phosphoric acid was added to about 1.2 g of the disaggregated and dried fibers, and then about 0.05 g of titanium dioxide was dispersed in a phosphoric acid solution and irradiation with ultraviolet rays was conducted at ambient temperature (5° C.) for 24 h with a 10 W antibacterial lamp produced by Toshiba.

The sample was then placed in a drier at 40° C. having silica gel placed therein and dried by heating for 24 h. This procedure of sample preparation was repeated 5 times and a total of 300 cc (solid fraction 30 g) was produced. The analytical values of the sample are shown in Table 1 below.

Analytical results obtained in Examples 1 to 3 [analysis was conducted in Japan Food Analysis Center]

As for the samples below, the solutions treated for 24 h at 40° C. (in a dried state with silica gel) were allowed to stay for several days and then analyzed.

Percents in parentheses (%) indicate a generation ratio produced by cellulose decomposition from which phosphoric acid and water are removed.
(*cellulose 1.12 g/85% phosphoric acid sample (20 cc) 32.902 g=3.4%)

TABLE 1

| Component | Paper + UV | Paper + Titanium oxide + UV | Rice straws + Titanium oxide + UV |
|---|---|---|---|
| Phosphoric acid | 67.0% | 57.2% | 64.2% |
| Water | 29.6% | 33.3% | 17.3% |
| Fibrous substance (cellulose) | — | — | 0.08% (2.3%) |
| Glucose* | 0.08% (2.35%) | 0.15% (4.4%) | 0.15% (4.4%) |
| Xylose* | 0.39% (11.5%) | 0.42% (12.4%) | 0.40% (11.8%) |
| Arabinose* | — | — | 0.07% (2.0%) |

*Sugars were analyzed by high-performance liquid chromatography

As follows from Table 1, in Examples 1 to 3, glucose and the like could be obtained at about 15%. The photocatalytic reaction of titanium oxide raised the glucose generation ratio by a factor of about 2.

In a case of rice straws, fiber disaggregation was incomplete and 2.3% cellulose remained undecomoposed.

It is preferred that the monosaccharide be separated from the obtained product including the monosaccharide such as glucose by an appropriate method such as UF filtration, and ethanol can thereafter be obtained by producing an aqueous solution of the separated monosaccharide and conducting ethanol fermentation of the aqueous solution by a well-known method.

The invention claimed is:

1. A method for producing a monosaccharide, comprising disaggregating and finely pulverizing a cellulose-based substance, mixing and dispersing the disaggregated and finely pulverized cellulose-based substance in a phosphoric acid solution, and decomposing the cellulose under irradiation with ultraviolet rays at a temperature of equal to or lower than 100° C., in the presence of a metal.

2. The method for producing a monosaccharide according to claim 1, comprising decomposing the cellulose-based substance in the presence of titanium dioxide.

3. The method according to claims 1, wherein the monosaccharide is glucose and/or xylose.

4. The method according to claims 1, wherein the cellulose-based substance is paper, wood, rice straw, chaff, old paper, dead leaves, wood from construction wastes, timber from forest thinning, or wind-fallen trees.

5. The method according to claim 1, wherein concentration of the phosphoric acid solution is 50% or more.

6. The method according to claim 1, wherein the metal is stainless steel.

* * * * *